(12) United States Patent
Jenkins (10) Patent No.: US 9,775,699 B2
(45) Date of Patent: Oct. 3, 2017

(54) ADJUSTABLE IMPLANT FOR THE TREATMENT OF URINARY INCONTINENCE

(71) Applicant: Kristina Yim Jenkins, Hudson, MA (US)

(72) Inventor: Kristina Yim Jenkins, Hudson, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 207 days.

(21) Appl. No.: 13/860,326

(22) Filed: Apr. 10, 2013

(65) Prior Publication Data

US 2013/0274545 A1 Oct. 17, 2013

Related U.S. Application Data

(60) Provisional application No. 61/623,766, filed on Apr. 13, 2012.

(51) Int. Cl.
*A61F 2/00* (2006.01)
*A61B 17/06* (2006.01)
*A61B 17/00* (2006.01)

(52) U.S. Cl.
CPC ...... *A61F 2/0045* (2013.01); *A61B 17/06109* (2013.01); *A61B 2017/00805* (2013.01); *F04C 2270/041* (2013.01)

(58) Field of Classification Search
CPC .... A61F 2/0045; A61F 2/0063; A61F 2/0004; A61F 2/0031; A61F 2/0036; A61F 2/00; A61B 2017/00805
USPC ...................................................... 600/30, 37
See application file for complete search history.

(56) References Cited

U.S. PATENT DOCUMENTS

| | | | |
|---|---|---|---|
| 2002/0183588 A1 | 12/2002 | Fierro | |
| 2003/0004580 A1* | 1/2003 | Sump | A61B 17/29 623/23.72 |
| 2004/0073234 A1 | 4/2004 | Chu et al. | |
| 2005/0256366 A1 | 11/2005 | Chu | |
| 2005/0267325 A1* | 12/2005 | Bouchier et al. | 600/37 |
| 2006/0025649 A1 | 2/2006 | Smith et al. | |
| 2006/0287571 A1 | 12/2006 | Gozzi et al. | |

(Continued)

FOREIGN PATENT DOCUMENTS

| | | |
|---|---|---|
| WO | 02/058564 A2 | 8/2002 |
| WO | 2013/155303 A1 | 10/2013 |

OTHER PUBLICATIONS

International Search Report and Written Opinion for PCT Patent Application No. PCT/US2013/036169, mailed Jun. 24, 2013, 14 pages.

(Continued)

*Primary Examiner* — Christine H Matthews
*Assistant Examiner* — Kaylee Wilson
(74) *Attorney, Agent, or Firm* — Brake Hughes Bellermann LLP (57) ABSTRACT

In an embodiment, the present invention discloses a medical assembly, including a sub-urethral implant, a strap, a dilator, and a suture. The implant includes a first end portion and a second end portion such that the strap is configured to be attached to the first end portion of the implant. The strap is attached to the implant through a weld. The strap is further configured to be coupled to the dilator. The suture can be coupled to the dilator.

20 Claims, 7 Drawing Sheets

(56) References Cited

U.S. PATENT DOCUMENTS

| | | |
|---|---|---|
| 2007/0038018 A1 | 2/2007 | Chu |
| 2007/0142835 A1* | 6/2007 | Green et al. .................... 606/72 |
| 2008/0004487 A1 | 1/2008 | Haverfield |
| 2008/0200751 A1* | 8/2008 | Browning .......... A61B 17/0401 600/30 |
| 2008/0287731 A1 | 11/2008 | Kuntz |
| 2009/0171143 A1* | 7/2009 | Chu et al. ....................... 600/37 |
| 2009/0209982 A1* | 8/2009 | Hoerstrup et al. ............ 606/151 |
| 2009/0221868 A1* | 9/2009 | Evans ................... A61F 2/0045 600/37 |
| 2010/0145140 A1 | 6/2010 | Chu |
| 2010/0197998 A1* | 8/2010 | Comiter et al. ............... 600/30 |
| 2010/0256443 A1* | 10/2010 | Griguol ................ A61F 2/0045 600/30 |
| 2011/0224698 A1* | 9/2011 | Deitch .............. A61B 17/0401 606/144 |
| 2013/0131441 A1* | 5/2013 | Chu ..................... A61F 2/0063 600/37 |

OTHER PUBLICATIONS

International Preliminary Report on Patentability for PCT Patent Application No. PCT/US2013/036169, mailed on Oct. 23, 2014, 8 pages.

\* cited by examiner

ADJUSTABLE IMPLANT FOR THE TREATMENT OF URINARY INCONTINENCE

CROSS-REFERENCE TO RELATED APPLICATION

This application is a Nonprovisional of, and claims priority to, U.S. Patent Application No. 61/623,766, filed on Apr. 13, 2012, entitled "ADJUSTABLE IMPLANT FOR THE TREATMENT OF URINARY INCONTINENCE", which is incorporated by reference herein in its entirety.

BACKGROUND

Field

The present invention generally relates to surgical devices and procedures, particularly devices and methods for the delivery of implants within a body of a patient.

Description of the Related Art

Urinary Incontinence (UI) is loss of bladder control, which may result in involuntary leakage of urine. Incontinence may be caused by various abnormalities in muscles and nerves that help in holding or releasing urine.

Various surgical and non-surgical techniques are adopted to treat disorders and damages associated with UI. One of them is an implant-based procedure. It involves placement of an implant under the bladder neck or the mid-urethra or any other location to provide a support platform. The surgical procedure includes introducing a medical device to deliver the implant inside the body of the patient through a small midline incision in the vaginal wall. The surgical procedure may also use placing needles into bodily tissues to facilitate placement of the implant underneath the urethra.

There is a need for an improved medical assembly that facilitates the delivery and implantation or placement of the implant within the body of the patient.

SUMMARY

In an embodiment, the present invention discloses a medical assembly, including a sub-urethral implant, a strap, a dilator, a suture. The implant includes a first end portion and a second end portion such that the strap is configured to be attached to the first end portion of the implant. The strap is attached to the implant through a weld. The strap is further configured to be coupled to the dilator. The suture can be coupled to the dilator.

In an embodiment, the present invention discloses a medical assembly, including a sub-urethral implant having a first end portion and a second end portion. The medical assembly further includes a tab. The tab has a top surface and a bottom surface. The top surface and the bottom surface do not define a lumen. The bottom surface is configured to be attached to a surface of the implant at the first end portion of the implant and the top surface is configured to contact a bodily tissue.

In an embodiment, the present invention discloses a method for placing an implant in a body of the patient. The method includes inserting the implant inside the body of the patient through a vaginal incision such that the implant is coupled to a strap at an end portion of the implant through a weld. The strap is further coupled to a dilator. The method further includes placing the implant under the urethra of the patient to provide support to the urethra. The method includes decoupling the strap from the implant. Decoupling can be done by pulling a suture coupled to the dilator. The method further includes removing the strap from the body of the patients.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components, as discussed in the subsequent text of the present invention, are referred with a point of reference. The point of reference, as used in this description, is a perspective of an operator. The operator may be a surgeon, a physician, a nurse, a doctor, a technician, and the like, who may perform the procedure of surgery through the body of the patient orifice or incision as described in the present invention. The term proximal refers to an area that is closest to the operator. The term distal refers to an area that is farthest from the operator. The patient can be a male, a female or any other mammal.

Figure 1:
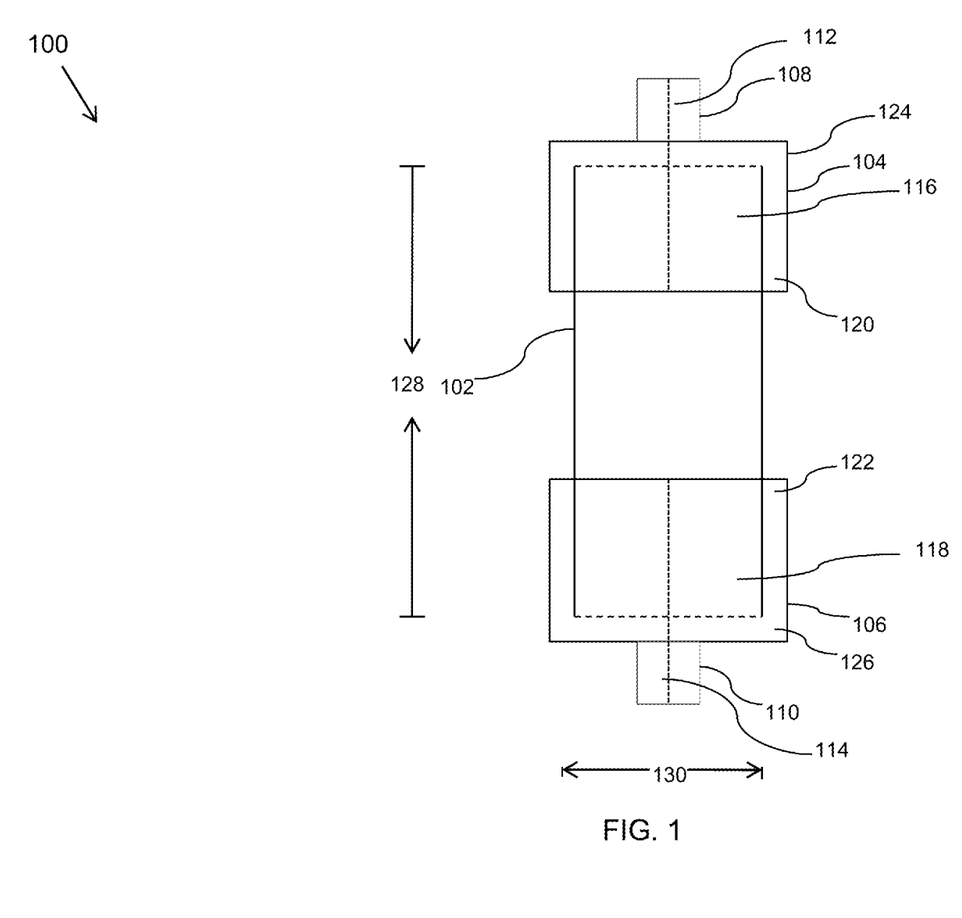
FIG. 1 is a schematic diagram of a medical assembly, in accordance with some embodiments of the present invention.

FIG. 1 is a schematic diagram of a medical assembly 100, in accordance with some embodiments of the present invention. The medical assembly 100 includes an implant 102, a first strap 104, a second strap 106, a first dilator 108, a second dilator 110, a first suture 112, and a second suture 114. In some embodiments, the implant 102 is a sub-urethral implant, as used hereafter. However, various other types of implants for various other purposes may also be employed.

The sub-urethral implant 102 (also referred to as implant 102) has a first end portion 116 and a second end portion 118 with a length 128 of the implant 102 extending between the first end portion 116 and the second end portion 118 longitudinally. In accordance with various embodiments, the implant 102 can have a variety of shapes such as rectangular, square, trapezoidal, and the like. In certain embodiments, the sub-urethral implant 102 is rectangular in shape and configured to be placed under a urethra.

The implant 102 further includes a first surface and a second surface that are separated by the thickness of the implant 102. The first surface and the second surface are on opposite sides such that they face away from one another when viewed in a horizontally lying plane or a vertically upright location.

In some embodiments, the implant 102 is made of a synthetic material such as a polymeric material and the like. In some embodiments, the implant 102 includes a polymeric mesh body. The mesh body may comprise a crisscrossed or chain link type design. In such designs, the fibers or strands of the mesh may be woven, linked, or otherwise connected, and may share the stress of a supported load. In other embodiments, the implant 102 includes a polymeric planar body without mesh cells and structures. Exemplary polymeric materials are polypropylene, polyester, polyethylene, nylon, PVC, polystyrene, and the like. In some embodiments, the implant 102 is made of a non-woven polymeric material. In some other embodiments, the implant 102 can be made of natural materials such as biologic material or a cadaveric tissue and the like. Exemplary natural materials are bovine dermis, porcine dermis, cellulose-based product, allograft, and bio-absorbable materials. In some embodiments, the implant is a mesh-based device made of polypropylene, or a biologic material or a combination thereof.

Additionally, in some embodiments, the implant 102 is stretchable and flexible to adapt movements along the anatomy of the human body. In some embodiments, the attributes such as softness, lightness, conformity, and strength are required in the implant 102 for efficient tissue repair and implantation.

In some embodiments, the length 128 and width 130 of the implant 102 may vary based on the intended use of the implant 102. The implant 102 can be of various sizes, shapes, and configurations depending on the intended use and locations of placement of the implant 102 within the body of the patient. The implant 102 can be shaped and sized according to the body tissues to be supported.

In some embodiments, the first strap 104 is configured to be attached to the first end portion 116 of the implant 102. In certain embodiments, the first strap 104 is a tab configured to be attached to the first end portion 116 of the implant 102. The first tab is a single layer tab 104 that does not enclose the first end portion 116 of the implant 102 completely. In certain embodiments, the first tab 104 can have a top surface and a bottom surface. The top surface of the first tab 104 makes contact with the bodily tissue, whereas the bottom surface attaches at the first end portion 116 of the implant 102. In some embodiments, the first tab 104 attaches to the first end portion 116 at the first surface of the implant 102 and shields a portion of only the first surface, whereas the second surface of the implant 102 remains un-shielded.

In some other embodiments, the second strap 106 is configured to be attached to the second end portion 118 of the implant 102. In certain embodiments, the second strap 106 is a tab 106 configured to be attached to the second end portion 118 of the implant 102. The second strap 106 is a single layer tab similar to the first tab 104 that does not enclose the second end portion 118 of the implant 102 completely. In certain other embodiments, the second tab 106 has a top surface and a bottom surface similar to the first tab 104. The second tab 106 attaches to the second end portion 118 at the first surface of the implant 102 and shields a portion of only the first surface whereas the second surface of the implant 102 remains un-shielded.

In some embodiments, the first tab 104 may cover a portion of the implant 102 other than the first surface. For example, the first tab 104 may cover a portion of one or more lateral edges of the implant in addition to the first surface. The first tab 104 may also cover some portion of the second surface of the implant 102 in some embodiments. It must be appreciated that the first tab 104 may cover the one or more lateral edges or some portion of the second surface of the implant even without actually forming a lumen in the first tab. In such cases, the single layered first tab itself may be just wrapped around the one or more edges or toward the second surface.

In some embodiments, the first tab 104 and the second tab 106 are configured to be attached to the implant 102 through a heat or an ultrasonic weld. The first end portion 116 of the implant 102 may be attached to a distal portion 120 of the first tab 104 and the second end portion 118 of the implant 102 may be attached to a distal portion 122 of the second tab 106. The end portions 116 and 118 of the implant 102 may, for example, be heat welded to or mounted on the first strap 104 and the second strap 106 using an intermediate structure, such as a band or a short segment of tube or heat-shrinkable material. Various other attachment mechanisms such as bonding, thermo-forming, welding, stitching, and the like may then be used to couple the first tab 104 and the second tab 106 with the implant 102.

The first tab 104 and the second tab 106 can have a variety of shapes such as rectangular, square, trapezoidal, and the like.

In some embodiments, the first strap 104 is a first sleeve 104 with a lumen to enclose the first end portion 116 of the implant 102 such that the first sleeve 104 encloses the first end portion 116 of the implant 102 within a space defined by the lumen. The second strap 106 is a second sleeve 106 with a lumen to enclose the second end portion 118 of the implant 102 such that the second sleeve 106 is configured to enclose the second end portion 118 of the implant 102.

In some embodiments, the first sleeve 104 and the second sleeve 106 are shaped in the form of hollow tubes or envelopes such that a hollow space within the sleeves 104 and 106 define lumens therein. The lumens of the first sleeve 104 and the second sleeve 106 are configured to receive the first portion and the second portion that can be the first end portion 116 and the second end portion 118 of the implant 102. The first end portion 116 and the second end portion 118 may be respectively disposed within the lumen of the first sleeve 104 and the second sleeve 106. In some embodiments, the implant 102 may be enclosed within the first sleeve 104 and the second sleeve 106. Alternatively, the implant 102 may be fixed to the first sleeve 104 and the second sleeve 106. The first sleeve 104 and the second sleeve 106 are together referred to as sleeves 104 and 106 hereafter for simplicity of the description. The lumens of the sleeves 104 and 106 may have width greater than the width 130 of the implant 102 at the first end portion 116 and the second end portion 118 that are configured to be covered by the sleeves 104 and 106. This may facilitate housing of the end portions 116 and 118 of the implant 102 within the lumens of the sleeves 104 and 106. In some other embodiments, proximal end portions 124 and 126 of the sleeves 104 and 106 are slightly tapered to allow easy withdrawal without catching tissues. In some other embodiments, the proximal end portions 124 and 126 of the sleeves 104 and 106 have openings or gaps such that the lumens of the sleeves 104 and 106 can be accessible through the openings or gaps. In some embodiments, the sleeves 104 and 106 can be made of resilient or flexible material such that the width of the lumens is smaller than the width 130 of the implant 102 in a normal condition. However, since the sleeves 104 and 106 can be configured to be stretched due to their flexible material, in some embodiments, the width of the lumens can be increased to an extent, enabling the receipt of the implant 102 within the lumens.

As described above, the first strap 104 can be the first tab or the first sleeve. Similarly, the second strap 106 can be the second tab or the second sleeve. The first strap 104 and the second strap 106 are together hereafter referred to as straps for simplicity of the description. In some embodiments, the first strap 104 and the second strap 106 are made of polymer and may be colored blue for visualization. In other embodiments, the straps 104 and 106 can be manufactured from an opaque or a transparent plastic film. The transparent plastic film enables visual examination of the implant 102. The straps 104 and 106 can be single or multiple ply. The straps 104 and 106 can be made by extruding or sandwiching two sheets of polymer together. In general, the straps 104 and 106 may be composed of any biocompatible material known in the art. Such materials may include, for example, polyethylene, PTFE, and EPTFE. The straps 104 and 106 may be composed of one material or, in some embodiments, the straps 104 and 106 may be made of a multilayered structure composed of one or more materials already mentioned. The straps 104 and 106 may have a length and width as per the requirements of implanting and positioning the implant 102 within the body of the patient, and may be flexible and easily manipulated when the implant 102 is disposed therein.

In some embodiments, the medical assembly 100 may further include the first dilator 108. The first dilator 108 is configured to be coupled to the proximal end portion 124 of the first strap 104. In some embodiments, the proximal end portion 124 of the first strap 104 wraps around completely to the first dilator 108 and attaches to it. In some other embodiments, the proximal end portion 124 of the first strap 104wraps around partially to the first dilator 108 and attaches to it.

In some embodiments, the medical assembly 100 may include the second dilator 110 similar to the first dilator 108. The second dilator 110 is configured to be coupled to the proximal end portion 126 of the second strap 106. In some embodiments, the first dilator 108 and the second dilator 110 can aid in easy insertion of the medical assembly 100 within the bodily tissues. In some embodiments, the first dilator 108 and the second dilator 110 may have through lumens. In other embodiments, the first dilator 108 and the second dilator 110 can be solid dilators 108 and 110 without any lumen therein.

In some embodiments, the first dilator 108 and the second dilator 110 are coupled respectively to the first strap 104 and the second strap 106 through heat bonding. In some other embodiments, various coupling mechanisms and fasteners other than heat bonding can be used to couple the first dilator 108 and the second dilator 110 with the first strap 104 and the second strap 106. In such embodiments, the coupling mechanisms such as sonification, gluing, stapling, stitching, shrink wrapping or the like can be used.

In some embodiments, the first dilator 108 and the second dilator 110 can be tubular in shape. In some other embodiments, the first dilator 108 and the second dilator 110 are further configured to be coupled to a delivery device. The delivery device can be a medical instrument that can be used to facilitate delivery of the medical assembly 100 including the implant 102 within the body of the patient. A few examples of the delivery devices may include the Boston Scientific Corporation Obtryx™, Lynx™, Advantage™, Prefyx™ delivery device or any other delivery device. In some embodiments, the first dilator 108 and the second dilator 110 are sufficiently small in diameter so as to provide a less invasive surgery. In some embodiments, the medical assembly 100 can be configured to couple with a suturing device. In some embodiments, the suturing device can be a Capio® device manufactured by Boston Scientific Corporation.

In some embodiments, the medical assembly 100 further includes the first suture 112 and the second suture 114. In some embodiments, the first suture 112 is coupled to the first dilator 108. In some embodiments, the coupling can be done through heat welding. In some other embodiments, various coupling mechanisms and fasteners other than heat bonding can be used to couple the first suture 112 with the first dilator 108. In such embodiments, the coupling mechanism and fasteners such as sonification, gluing, stapling, stitching, shrink wrapping or the like can be used.

In some embodiments, the first suture 112 is configured to pass through the lumen within the first dilator 108. In some embodiments, the first suture 112 runs across the lumen of the first dilator 108 and past the first dilator 108 to the first strap 104. The first suture 112 then passes through or along or over some portion of the first end portion 116 of the implant 102, thereby coupling the first strap 104 and the implant 102 with the dilators 108 and 110. In accordance with some embodiments, the second suture 114 is configured to pass through the second dilator 110 and couples the second strap 106 and the implant 102 with the dilators 108 and 110 in a similar manner as described above for the first suture 112.

In some embodiments, the first suture 112 and the second suture 114 can be one of a thread, a medical suture, a filament, a rope, and the like. In some embodiments, the first suture 112 and the second suture 114 can be a monofilament suture or a braided suture. In some embodiments, the first suture 112 and the second suture 114 can be integral parts of a single member such as a thread. In some other embodiments, the first suture 112 and the second suture 114 can be discrete members that are not coupled or are not parts of a single member or a thread.

The first suture 112 and the second suture 114 may be made of biological materials and/or synthetic materials. The first suture 112 and the second suture 114 may be strong enough to hold both the straps 104 and 106, and the implant 102 securely. In some embodiments, the first suture 112 and the second suture 114 are monofilament. In other embodiments, the first suture 112 and the second suture 114 are multifilament.

In some embodiments, the straps 104 and 106 and the dilators 108 and 110 can be coupled through elements such as adhesives, bonding agents, mechanical fasteners (e.g., a medical grade plastic clip), and the like.

Figure 2A:
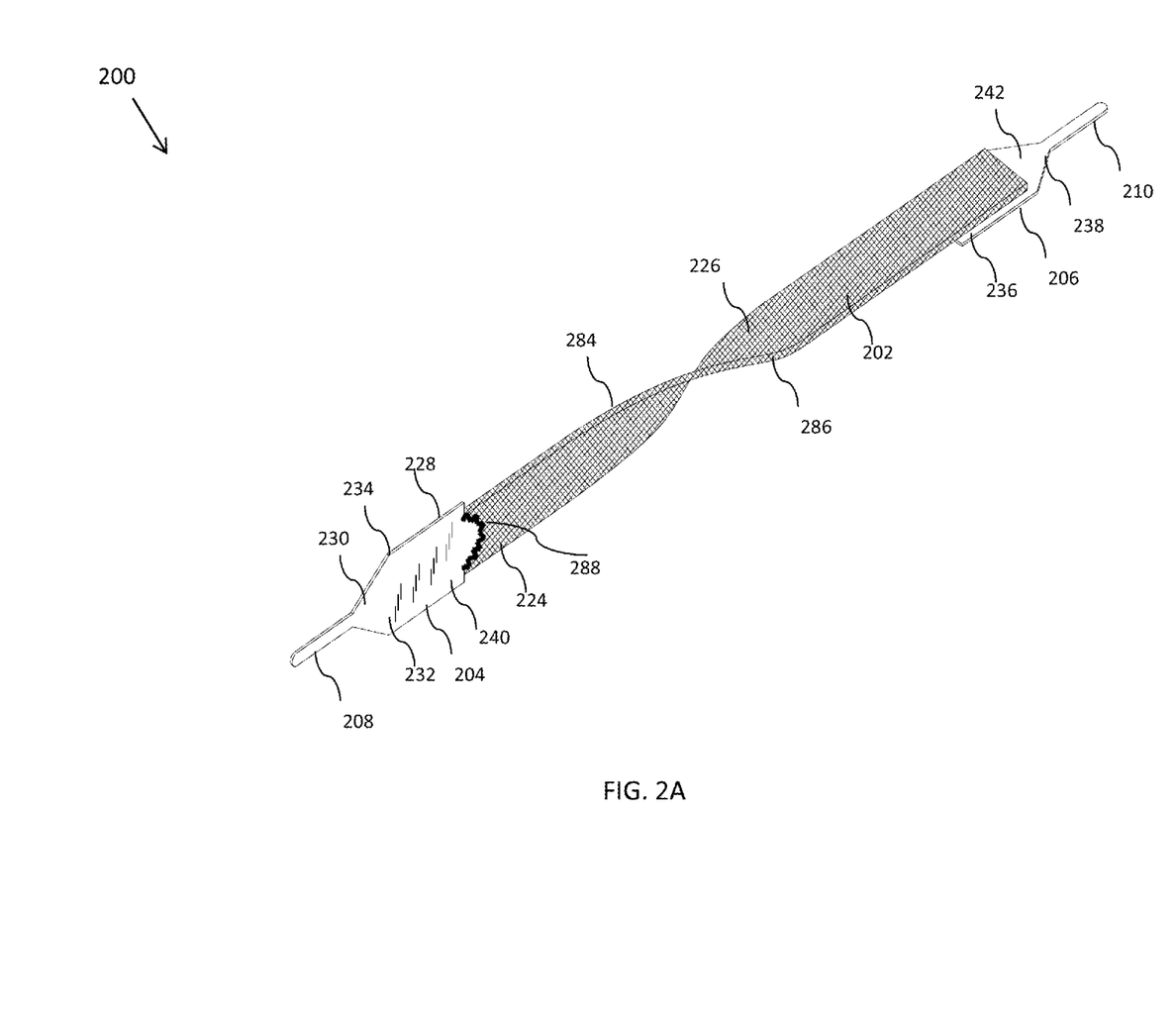
FIGS. 2A-2B are different views of a medical assembly, in accordance with some embodiments of the present invention.
Figure 2B:
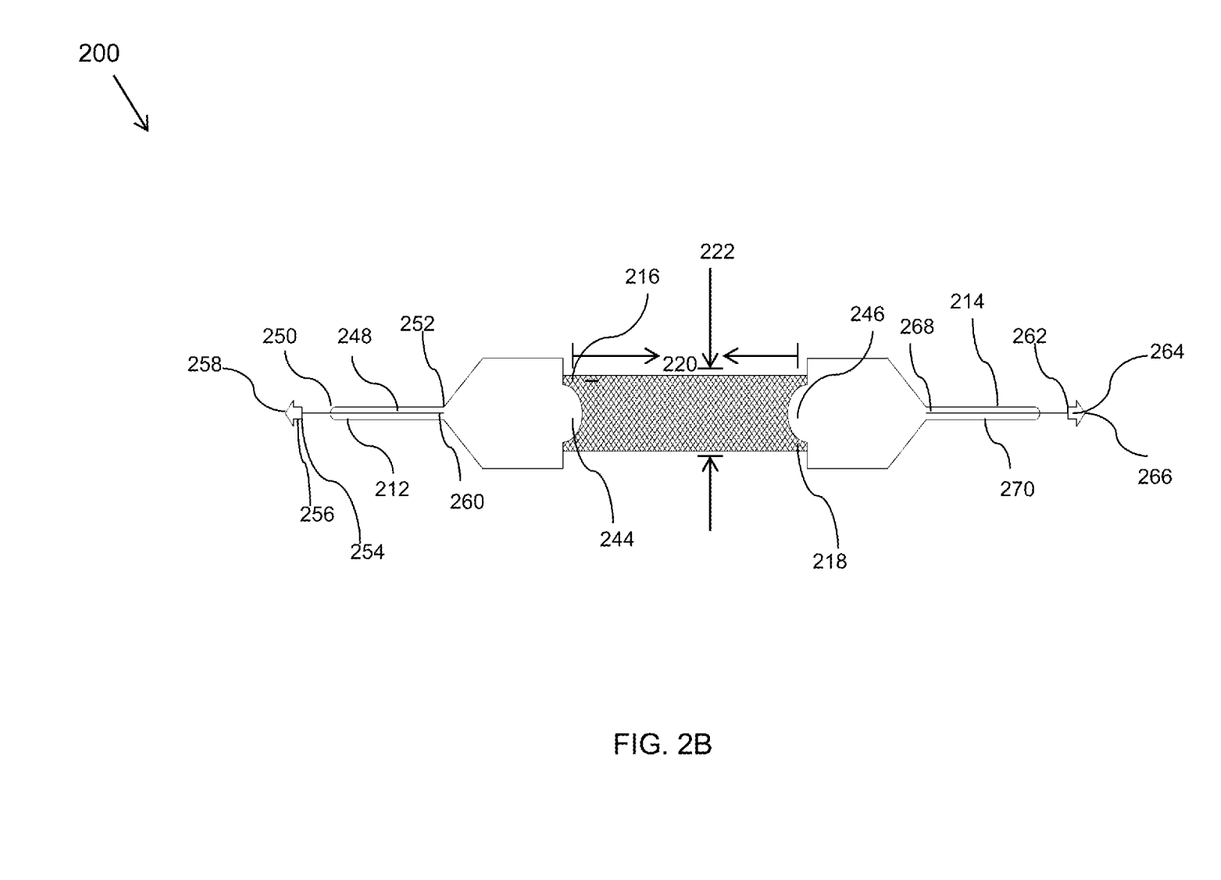

FIGS. 2A-2B illustrate a medical assembly 200, in accordance with an embodiment of the present invention. Referring now to FIGS. 2A-2B, the medical assembly 200 is described.

FIG. 2A is a perspective view of the medical assembly 200 in accordance with an embodiment of the present invention. The medical assembly 200 includes an implant 202, a first strap 204, a second strap 206, a first dilator 208, and a second dilator 210. The medical assembly 200 may also include a first suture 212, and a second suture 214 (as shown in FIG. 2B).

The sub-urethral implant 202 (also referred to as implant 202) has a first end portion 216 and a second end portion 218 with a length 220 of the implant 202, extending between the first end portion 216 and the second end portion 218 longitudinally. In some embodiments, the sub-urethral implant 202 is rectangular in shape and configured to be placed under a urethra. Additionally, in some embodiments, the implant 202 is stretchable and flexible to adapt movements along the anatomy of the human body. In some embodiments, the attributes such as softness, lightness, conformity, and strength are required in the implant 202 for efficient tissue repair and implantation.

In some embodiments, the length 220 and width 222 of the implant 202 may vary based on the intended use of the implant 202. The implant 202 can be of various sizes, shapes, and configurations depending on the intended use and locations of placement of the implant 202 within the body of the patient. In some embodiments, the implant 202 can be rectangular in shape.

The implant 202 further includes a first surface 224 and a second surface 226 that are separated by a thickness of the implant 202. The first surface 224 and the second surface 226 are on opposite sides such that they face away from one another when viewed in a horizontally lying plane or a vertically upright location.

The first strap 204 is configured to be attached to the first end portion 216 of the implant 202. In certain embodiment, the first strap 204 is a single layer tab 204. The first tab 204 does not enclose the first end portion 216 of the implant 202 completely. The first tab 204 is configured to be attached to a first surface 224 of the implant 202 at the first end portion 216. In certain embodiments, the first tab 204 has a first distal end portion 228 and a first proximal end portion 230. In some embodiments, as shown, the first distal end portion 228 is in the shape of a substantially half circle configured to be coupled with the first end portion 216 of the implant 202. In some embodiments, the first tab 204 has a top surface 232 and a bottom surface 234. The top surface 232 of the first tab 204 makes contact with a bodily tissue whereas the bottom surface 234 attaches at the first end portion 216 of the implant 202. In some embodiments, the first tab 204 attaches to the first end portion 216 at the first surface 224 of the implant 202 and shields a portion of only the first surface 224, whereas the second surface 226 of the implant 202 remains un-shielded. In some other embodiments, the second strap 206 is configured to be attached to the second end portion 218 of the implant 202. In certain embodiments, the second tab 206 has a second distal end portion 236 and a second proximal end portion 238. The second distal end portion 236 is in the form of a substantially half circle configured to be coupled with the second end portion 218 of the implant 202. In some embodiments, the second strap 206 is a tab 206 similar to the first tab 204 configured to be attached to the second end portion 218 of the implant 202. The second tab 206 is a single layer tab 206 similar to the first tab 204 that does not enclose the second end portion 218 of the implant 202 completely. The second tab 206 has a top surface 240 and a bottom surface 242 similar to the first tab 204. The second tab 206 attaches to the second end portion 218 at the first surface 224 of the implant 202 and shields a portion of only the first surface 224, whereas the second surface 226 of the implant 202 remains un-shielded.

In some embodiments, the first tab 204 may cover some portion of the implant 202 other than the first surface 224 of the implant 202. In such embodiments, the first tab 204 may cover some portion of a first edge 284 of the implant 102. In some other embodiments, the first tab 204 may cover some portion of a second edge 286 of the implant 102. In some embodiments, the first tab 104 may also cover some portion of the second surface 226. The second tab 206, similar to the first tab 204, may also cover the first edge 284, the second edge 286 and some portion of the second surface 226.

In some embodiments, the first tab 204 and the second tab 206 are configured to be attached to the implant 202 through a heat or an ultrasonic weld 288. The first end portion 216 of the implant 202 may be attached to the first distal end portion 228 of the first tab 204 and the second end portion 218 of the implant 202 may be attached to the second distal end portion 236 of the second tab 206. The first distal end portion 228 of the first tab 204 and the second distal end portion 236 of the second tab 206 may include a first protruded portion 244 and a second protruded portion 246 such that the first protruded portion 244 and the second protruded portion 246 are in the form of half circles as illustrated in FIG. 2B. FIG. 2B provides a perspective view of the medical assembly 200 in another orientation. In some embodiments, the first protruded portion 244 and the second protruded portion 246 can be heat welded with the implant 202. The heat welding can be strong enough to keep the first tab 204 and the second tab 206 and the implant 202 coupled together, but weak enough to decouple the first tab 204 and the second tab 206 from the implant 202 on pulling of the first tab 204 and the second tab 206. In some embodiments, the first distal end portion 228 and the second distal end portion 236 are tapered such that the tapered ends facilitate easy withdrawal of the first tab 204 and the second tab 206 without catching tissues.

The first end portion 216 and the second end portion 218 of the implant 202 may, for example, be heat welded to or mounted on the first strap 204 and the second strap 206 using an intermediate structure, such as a band or a short segment of tube or heat-shrinkable material. Various attachment mechanisms such as bonding, thermo-forming, welding, stitching, and the like may also be used to couple the first strap 204 with the implant 202.

The medical assembly 200 may further include the first dilator 208. The first dilator 208 is configured to be coupled to the proximal end portion 230 of the first strap 204. In some embodiments, the first strap 204 wraps around completely and attaches to the first dilator 208. In some other embodiments, the first strap 204 wraps around partially and attaches to the first dilator 208.

In some embodiments, the medical assembly 200 may include the second dilator 210 that can be similar to the first dilator 208. The second dilator 210 is configured to be coupled to the proximal end portion 238 of the second strap 206. In some embodiments, the first dilator 208 and the second dilator 210 can be dilators that may aid in easy insertion of the medical assembly 200 within the bodily tissues. In some embodiments, the first dilator 208 and the second dilator 210 may have through lumens 248 and 270.

In some embodiments, the first dilator 208 and the second dilator 210 are coupled respectively to the first strap 204 and the second strap 206 through heat bonding. In some other embodiments, various coupling mechanisms and fasteners other than heat bonding can be used to couple the first dilator 208 and the second dilator 210 with the first strap 204 and the second strap 206. In such embodiments, the coupling mechanisms such as sonification, gluing, stapling, stitching, shrink wrapping or the like can be used.

Figure 4:
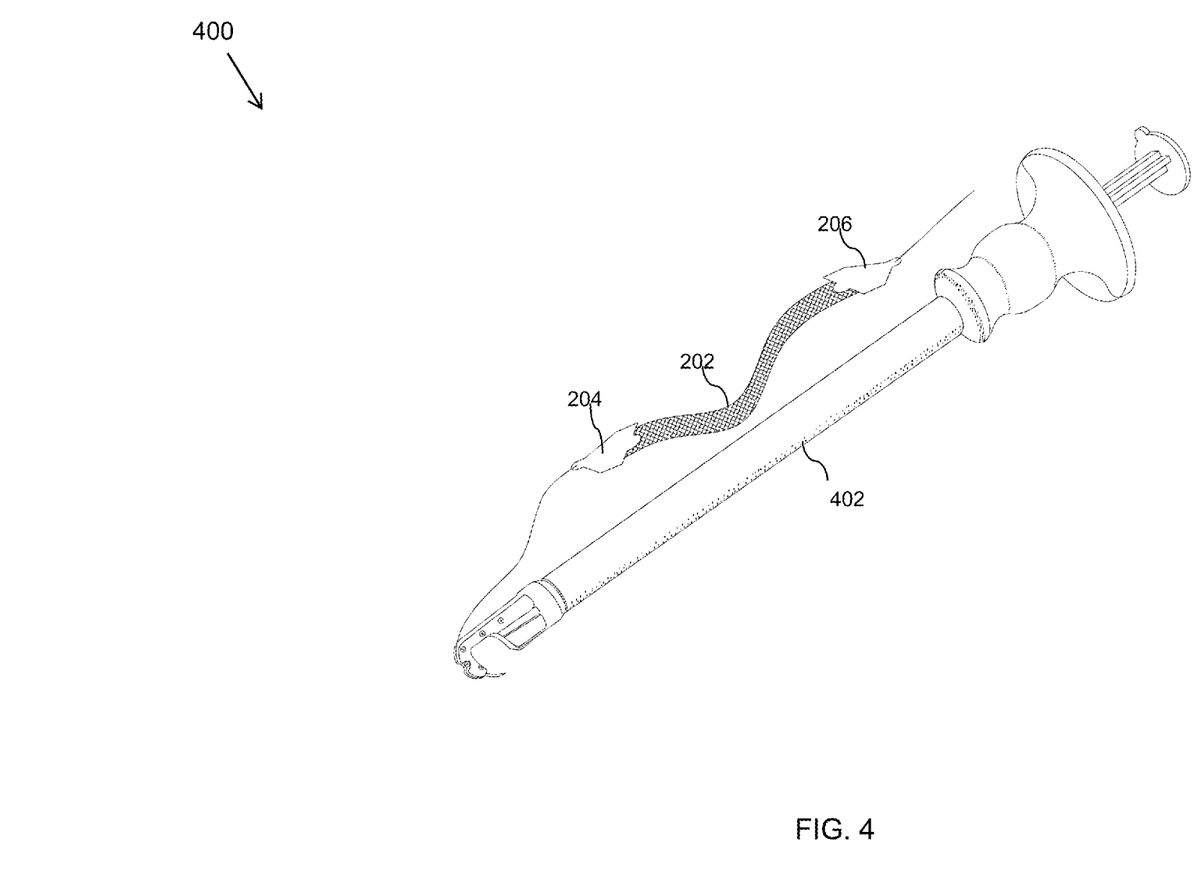
FIG. 4 illustrates coupling of a medical assembly with a suturing device or placement of an implant in a body of a patient, in accordance with an embodiment of the present invention.

In some embodiments, the first dilator 208 and the second dilator 210 are further configured to be coupled to a delivery device. The delivery device can be a medical instrument that can be used to facilitate delivery of the medical assembly 200, including the implant 202 within the body of the patient. A few examples of the delivery devices may include the Boston Scientific Corporation Obtryx™, Lynx™, Advantage™, Prefyx™ delivery device or any other delivery device. In some embodiments, the medical assembly 200 can be configured to couple with a suturing device. In some embodiments, the suturing device can be a Capio® device 402 as shown in FIG. 4 manufactured by Boston Scientific Corporation.

The medical assembly 200 may further include the first suture 212 and the second suture 214. In some embodiments, the first suture 212 is coupled to the first dilator 208. In some embodiments, the coupling can be done through heat welding. In some other embodiments, the coupling can be done by draping the first suture 212 around an outer surface of the first dilator 208. In some embodiments, the first suture 212 can be glued at the outer surface of the first dilator 208 to couple the first dilator 208 with the first suture 212. In various other embodiments, the first suture 212 can be coupled to the first dilator 208 by various other coupling techniques.

In some embodiments, the first suture 212 is configured to pass through the lumen 248 within the first dilator 208. The first suture 212 passes through the first dilator 208 such that the first suture 212 runs through a first opening 250 to a second opening 252 of the first dilator 208.

In some embodiments, a first end 254 of the first suture 212 is configured to be coupled to a first needle 256. In some embodiments, the first needle 256 can be made of a material selected at least from the group consisting of a plastic, a bio absorbable, a radiopaque, and a medical-grade stainless steel. In some embodiments, the first needle 256 has a tip portion 258 configured to be fixed to a bodily tissue and configured to anchor the implant 202 with the bodily tissue upon placement. In some embodiments, the dart or anchors may be attached to the needle or dilators. In some embodiments, a second end 260 of the first suture 212 is configured to pass through or across or over the first dilator 208. In some embodiments, the second end 260 of the first suture 212 can pass through the lumen 248 of the first dilator 208 as discussed above. In such embodiments, the first suture 212 can be suspended within the lumen 248 of the first dilator 208.

The medical assembly 200 further includes the second suture 214. The second suture 214 is configured to pass through or across or over the second dilator 210 in a similar manner as described above for the first suture 212.

In some embodiments, a first end 262 of the second suture 214 is configured to be coupled to a second needle 264. In some embodiments, the second needle 264 can be made of a material selected at least from the group consisting of a plastic, a bio absorbable, a radiopaque, and a medical grade stainless steel. In some embodiments, the second needle 264 has a tip portion 266 configured to be fixed to a bodily tissue and configured to anchor the implant 202 with the bodily tissue upon placement. In some embodiments, the dart or anchors may be attached to the needle or dilators. In some embodiments, a second end 268 of the second suture 214 is configured to pass through or across or over the second dilator 210. In some embodiments, the second end 268 of the second suture 214 can pass through the lumen 270 of the second dilator 210 as discussed above. In such embodiments, the second suture 214 can be suspended within the lumen 270 of the second dilator 210.

Figure 3:
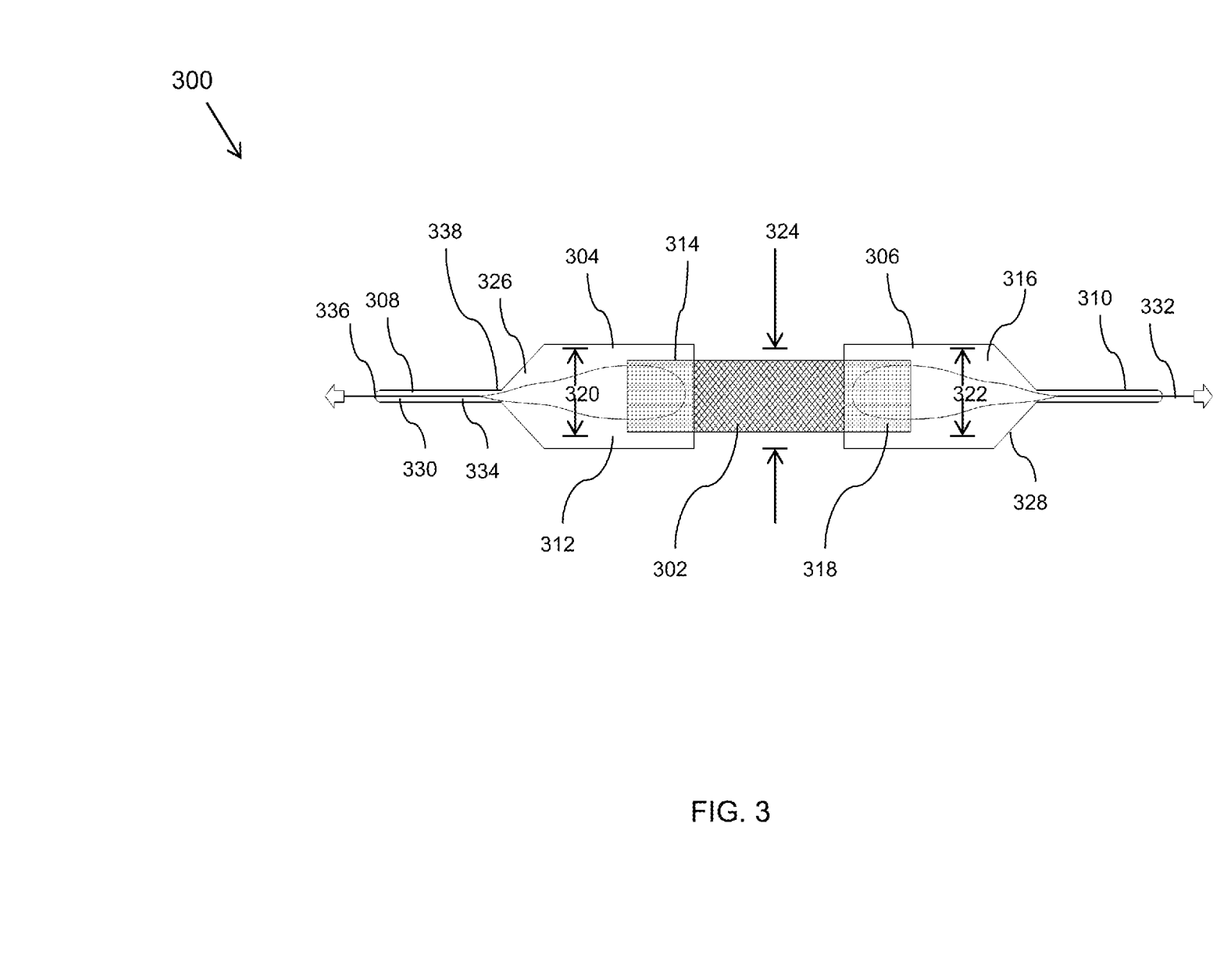
FIG. 3 illustrates a medical assembly, in accordance with some embodiments of the present invention.

FIG. 3 illustrates a medical assembly 300, in another embodiment. The medical assembly 300 includes an implant 302, a first strap 304, a second strap 306, a first dilator 308, and a second dilator 310.

In some embodiments, the first strap is a first sleeve 304 with a lumen 312 to enclose the first end portion 314 of the implant 302 such that the first sleeve 304 encloses the first end portion 314 of the implant 302 within a space defined by the lumen 312. The second strap 306 is a second sleeve 306 with a lumen 316 to enclose the second end portion 318 of the implant 302 such that the second sleeve 306 is configured to enclose the second end portion 318 of the implant 302.

In some embodiments, the first sleeve 304 and the second sleeve 306 are shaped in the form of hollow tubes or envelopes such that a hollow space within the sleeves 304 and 306 define lumens 312 and 316 therein. The lumens 312 and 316 of the first sleeve 304 and the second sleeve 306 are configured to receive the first portion and the second portion that can be the first end portion 314 and the second end portion 318 of the implant 302. The first end portion 314 and the second end portion 318 may be respectively disposed within the lumens 312 and 316 of the first sleeve 304 and the second sleeve 306. In some embodiments, the implant 302 may be free-floating within the first sleeve 304 and the second sleeve 306. Alternatively, the implant 302 may be fixed to the first sleeve 304 and the second sleeve 306. The first sleeve 304 and the second sleeve 306 are together referred to as sleeves 304 and 306 hereafter for simplicity of the description.

The lumens 312 and 316 of the sleeves 304 and 306 have widths 320 and 322 that are greater than the width 324 of the implant 302 at the first end portion 314 and the second end portion 318 that are configured to be covered by the sleeves 304 and 306. This may facilitate housing of the end portions 314 and 318 of the implant 302 within the lumens 312 and 316 of the sleeves 304 and 306. In some other embodiments, distal end portions 326 and 328 of the sleeves 304 and 306 are slightly tapered to allow easy withdrawal without catching tissues. In some other embodiments, the distal end portions 326 and 328 of the sleeves 304 and 306 have openings or gaps such that the lumens 312 and 316 of the sleeves 304 and 306 are accessible through the openings or gaps. In some embodiments, the sleeves 304 and 306 can be made of resilient or flexible material such that the widths 320 and 320 are smaller than the width 324 of the implant 302 in a normal condition. However, since the sleeves 304 and 306 are configured to be stretched due to their flexible material, the widths 320 and 322 can be increased to an extent, enabling the receipt of the implant 302 within the lumen 312 and 316.

In some embodiments, the medical assembly 300 can include a first suture 330 and a second suture 332. The first suture 330 can couple the first sleeve 304 and the implant 302 with the dilators 308 and 310. In some embodiments, the first suture 330 runs across a lumen 334 of the first dilator 308 from the first opening 336 to the second opening 338 of the first dilator 308 and past the first dilator 308 to extend over or into or through the first sleeve 304 such that the first suture 330 couples the first sleeve 304 with the implant 302. In accordance with these embodiments, the suture can run across or within or into the strap and the implant 302 in various designs and layout. For example, in an embodiment, the second suture 332 can form a loop kind of structure while coupling the implant 302 with the second strap 306 as shown in FIG. 3. In other embodiments, the second suture 332 can run across or into the second strap 306 and the implant 302 in a linear manner. In some other embodiments, where the first dilator 308 does not include a lumen 334, the first suture 330 may run along or over the first dilator 308 (such as in a wrapped manner) and past the first dilator 308 to extend over or into or through the first sleeve 304 such that the first suture 330 couples to the first sleeve 304. The second suture 332 may also be deployed in a similar manner in some embodiments.

Figure 5:
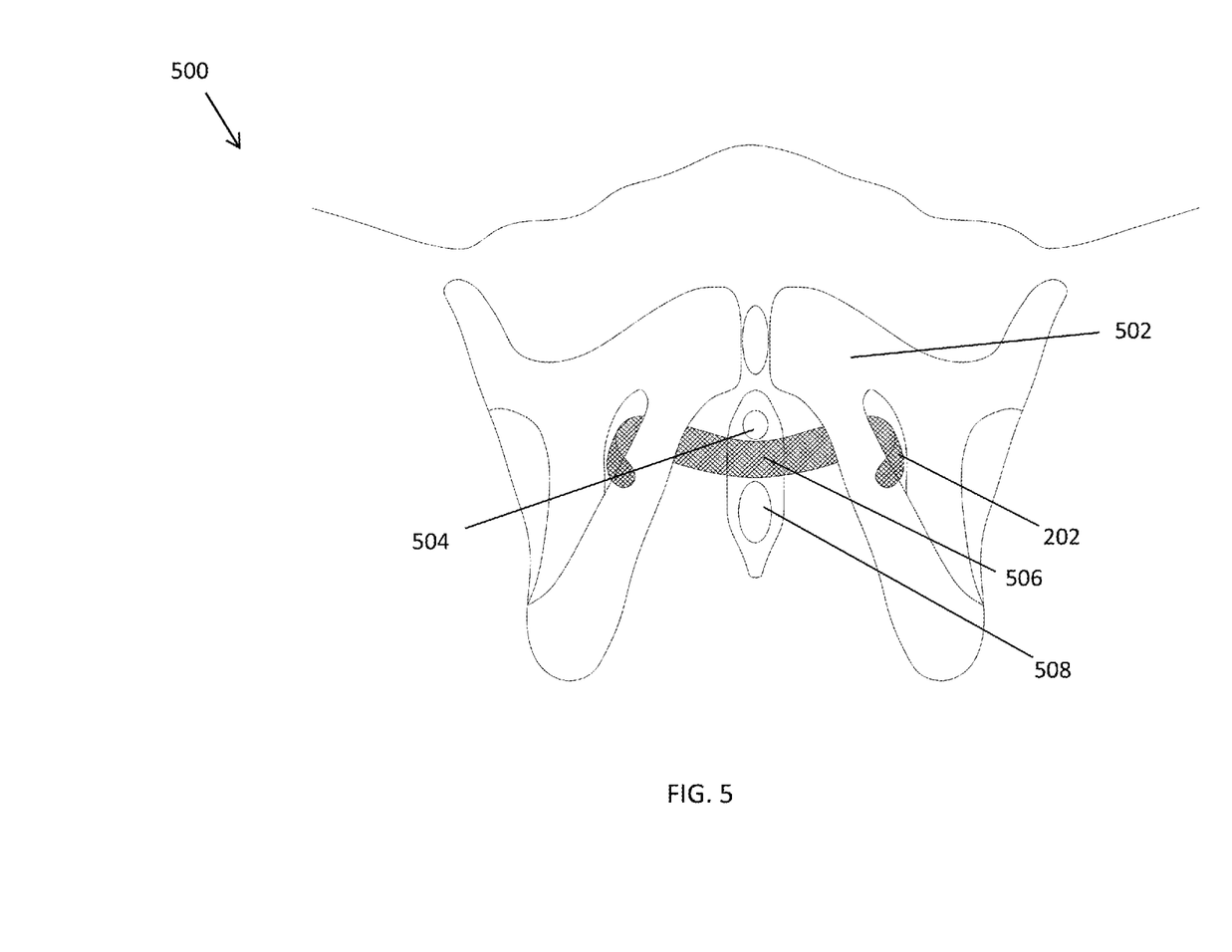
FIG. 5 illustrates placement of the implant within a body of the patient, in accordance with an embodiment of the present invention.

FIG. 5 illustrates placement of the implant 202 in a body of the patient, in accordance with an embodiment of the present invention. After the implant 202 is inserted and disposed inside the body, the first needle 256 and the second needle 264 are secured to the bodily tissue such as in or through the obturator muscles or membrane. The securing of the implant 202 to the obturator muscles (transobturator approach) is illustrated in FIG. 5. In certain other embodiments, the first needle 256 and the second needle 264 can be secured or fixed to other bodily tissues also such as close to a pubic bone 502 or sacrum of the patient. The first needle 256 and the second needle 264 are secured to the bodily tissues. For example, the first needle 256 is secured to a first bodily tissue and the second needle 264 is secured to a second bodily tissue, and the implant 202 is placed at a desired position. The needles 256 and 264, along with the first dilator 208, second dilator 210, first strap 204, and the second strap 206, can be removed once the implant 202 is appropriately positioned, thereby only leaving the implant 202 behind for fixation inside the body.

Figure 6:
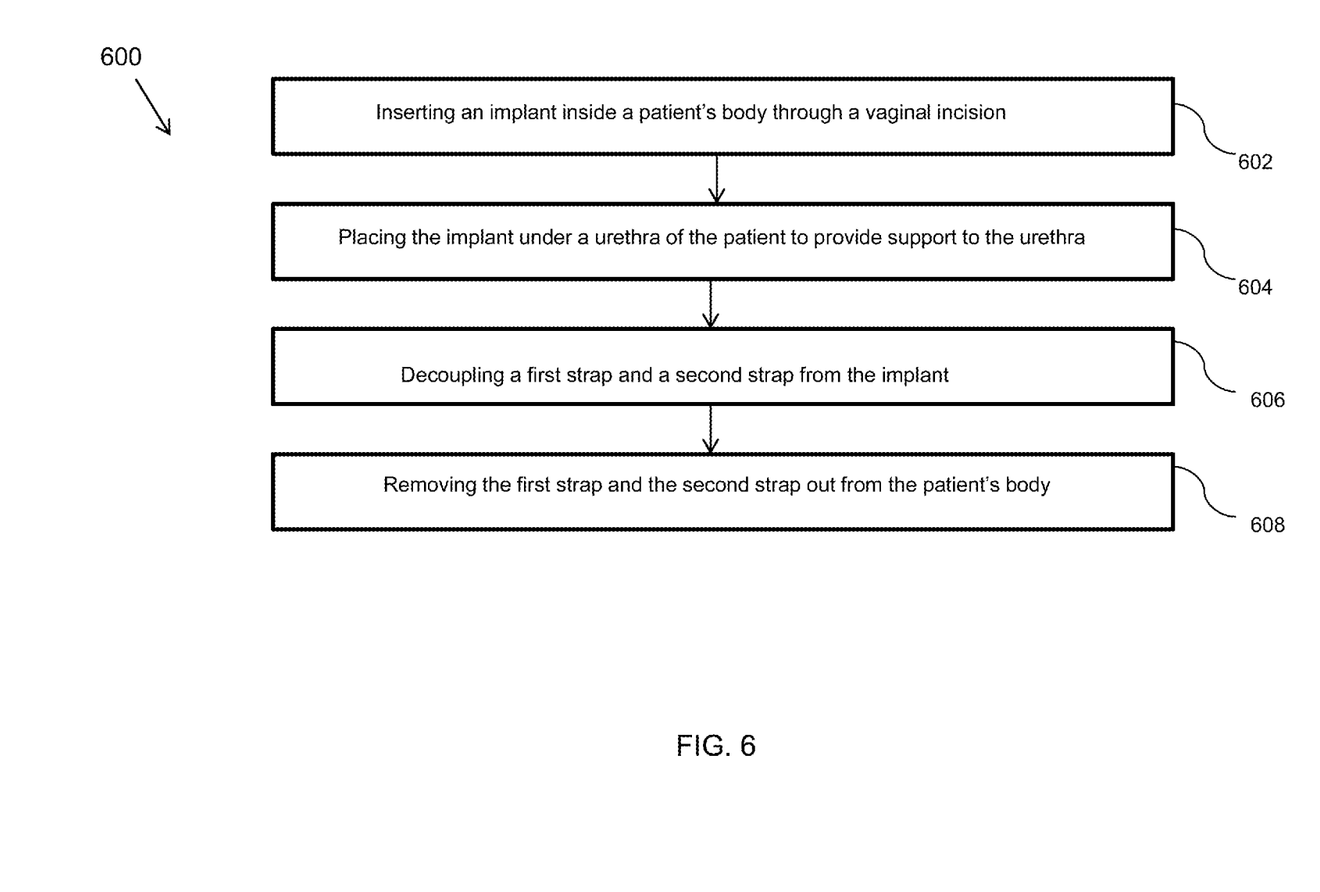
FIG. 6 illustrates a flow chart depicting a method of delivery of a medical assembly, in accordance with an embodiment of the present invention.

FIG. 6 illustrates a flow chart representing a method 600 for the delivery of the medical assembly 200 in a body of the patient, in accordance with an embodiment of the present invention. Referring to FIG. 5 and FIG. 6 now, the method 600 for the delivery of the medical assembly 200 in the body of the patient is described.

The method 600 includes inserting the medical assembly 200 inside the body of the patient through a vaginal incision 508 at step 602. The method may also include creating the vaginal incision 508 for inserting the medical assembly 200 inside the body of the patient. In some embodiments, the medical assembly 200 includes the implant 202 coupled to the first strap 204 and the second strap 206 at either end portions 216 and 218 of the implant 202 through the heat or the ultrasonic weld 288. The first strap 204 and the second strap 206 can further be coupled to the first dilator 208 and the second dilator 210 respectively. In some embodiments, the first dilator 208 and the second dilator 210 can be placed into an obturator muscle. In some embodiments, the implant 202 can be a sub-urethral implant 202.

The method 600 further includes placing the implant 202 under a urethra 504 (shown in FIG. 5) of the patient at step 604 to provide support to the urethra 504. In accordance with various embodiments, since the first end portion 216 and the second end portion 218 of the implant 202 are covered by the first strap 204 and the second strap 206, therefore, only some portion of the implant 202 is un-shielded. In some embodiments, the un-shielded portion is a middle portion 506 (shown in FIG. 5) of the implant 202 that contacts bodily tissues directly. The interaction of the un-shielded portion of the implant 202 with the bodily tissues underneath the urethra 404 provides a physician with a visual and a tactile feedback through a mid-line or skin incision.

In some embodiments, the position of the implant 202 may be adjusted. The implant 202 can be adjusted in a manner that the implant 202 contours an outer surface of the urethra 504 that is in contact with the implant 202. The physician may further adjust tension of the implant 202 to readjust the implant 202 to provide it an appropriate tension for effective placement and treatment. In some embodiments, the physician may tension the implant 202 by adjusting positions of the first dilator 208 and the second dilator 210. The tensioning can be done by re-locating the first dilator 208 and the second dilator 210 from a first position to a second position.

After tensioning the implant 202, the first strap 204 and the second strap 206 are released or decoupled from the implant 202 at step 606.

In some embodiments, the first strap 204 and the second strap 206 are coupled to the first end portion 216 and the second end portion 218 of the implant 202 through welding techniques. The weld 288 is strong enough to couple the straps 204 and 206 and the implant 202 together, but weak enough to decouple the first strap 204 and the second strap 206 from the implant 202 on pulling of the first strap 204 and the second strap 206. In some embodiments, the physician may put his finger on the middle portion 406 i.e. the un-shielded portion of the implant 202 to hold the implant 202 under the urethra through a frictional force. The physician may then pull the first strap 204 and the second strap 206 while holding the finger at the middle portion 406 of the implant 202. In some embodiments, the weld 288 is strong enough that the pulling force applied by the physician while insertion doesn't break the weld 288 between the implant 202 and the straps 204 and 206 but is not strong enough to sustain the pulling force applied by the physician externally on the straps 204 and 206 for removal of the straps 204 and 206 after implant placement. This may cause that straps 204 and 206 to get decoupled. The pulling force applied by the physician on the straps 204 and 206 is strong enough to break the weld 288 and hence decouple the first strap 204 and the second strap 206 from the implant 202. Also, the frictional force is more than the pulling force and is capable of holding the implant 202 under the urethra 404 against the pulling force. The first strap 204 and the second strap 206 can then be removed from the body of the patient at step 608 after decoupling from the implant 202.

In some embodiments, the first strap 204 and the second strap 206 can be coupled to the first end portion 216 and the second end portion 218 of the implant 202 through the first suture 212 and the second suture 214. In such embodiments, the first strap 204 can be released by cutting the first suture 212 and removed by pulling the first suture 212 that pass through lumen 248 within the first dilator 208 and attached to the first strap 204. The second strap 206 can be released by cutting the second suture 214 and removed by pulling the second suture 214 in a manner similar to the first suture 212. After decoupling, the straps 204 and 206 can then be removed. After removal of the straps 204 and 206, the vaginal incision 408 can be closed.

In some embodiments, the method may also include removing the first dilator 208 and the second tubular 210 member from the body of the patient leaving the implant 202 within the body of the patient.

It must be appreciated that the above description provides an exemplary treatment procedure, while in some other embodiments; the medical assembly and the method described above can be used for other treatment purposes such as for various other types of pelvic floor disorders. In accordance with the described and/or other embodiments, a transobturator sling or a surgical approach may be utilized.

In some embodiments, a medical assembly includes a sub-urethral implant having a first end portion and a second end portion; a strap configured to be attached to the first end portion of the implant such that the strap is attached to the implant through a weld; a dilator configured to be coupled to the strap; and a suture coupled to the dilator.

In some embodiments, the strap is a first strap, the medical assembly further includes a second strap configured to be attached to the second end portion of the implant.

In some embodiments, the strap includes a top surface and a bottom surface. The top surface and the bottom surface not defining a lumen. The bottom surface configured to be attached to a surface of the implant at the first end portion.

In some embodiments, the strap is a sleeve that defines a lumen to enclose the first end portion of the implant.

In some embodiments, the dilator is a first dilator. The medical assembly further includes a second dilator configured to be coupled to the second strap.

In some embodiments, the suture is a first suture. The medical assembly further including a second suture coupled to the second dilator.

In some embodiments, the assembly includes a first needle and a second needle configured to be coupled to the first dilator and the second dilator through the first suture and the second suture.

In some embodiments, the weld is one of a heat weld and an ultrasonic weld.

In some embodiments, the implant is rectangular in shape.

In some embodiments, the implant is a mesh-based device made of polypropylene, or a biologic material or a combination thereof.

In some embodiments, a medical assembly includes a sub-urethral implant having a first end portion and a second end portion; and a tab including a top surface and a bottom surface, the tab being devoid of a lumen, the bottom surface configured to be attached to a surface of the implant at the first end portion of the implant and the top surface configured to contact a bodily tissue.

In some embodiments, the tab is configured to be attached to the surface of the implant at the first end portion through a heat or an ultrasonic weld.

In some embodiments, the tab is a first tab, the medical assembly further including a second tab including a top surface and a bottom surface, the top surface and the bottom surface not defining a lumen, the bottom surface configured to be attached to a surface of the implant at the second end portion of the implant through a head or an ultrasonic weld.

In some embodiments, the medical assembly includes a first dilator and a second dilator respectively coupled to the first tab and the second tab.

In some embodiments, the medical assembly includes a first suture and a second suture respectively coupled to the first dilator and the second dilator.

In some embodiments, the sub-urethral implant is rectangular in shape and configured to be placed under urethra.

In some embodiments, a method for placing a sub-urethral implant in a body of a patient includes inserting the implant inside the body of the patient through a vaginal incision, the implant coupled to a strap at an end portion of the implant through a weld, the strap further coupled to a dilator; placing the implant under a urethra of the patient to provide support to the urethra; decoupling the strap from the implant by pulling a suture coupled to the dilator; and removing the strap out from the patient's body.

In some embodiments, the method includes creating an incision inside a patient's body.

In some embodiments, the strap includes a top surface and a bottom surface, the top surface and the bottom surface not defining a lumen, the bottom surface configured to be attached to a surface of the implant at the first end portion.

In some embodiments, the strap is a sleeve that defines a lumen to enclose the end portion of the implant, the sleeve configured to be attached to the end portion of the implant through a heat or an ultrasonic weld.

In some embodiments, the method includes adjusting tension of the implant by adjusting position of the dilator, dilator, or the implant.

In some embodiments, the method includes removing the dilator from the patient's body leaving the implant within the patient's body.

In some embodiments, the implant is rectangular in shape.

In some embodiments, the method includes closing the vaginal incision.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A medical assembly for treatment of urinary incontinence, the medical assembly comprising:
   an implant having a first end portion and a second end portion, the implant including a mesh material;
   a tab configured to be removably attached to the first end portion of the implant, the tab including a non-mesh material, the tab being a single layer tab devoid of a lumen, the tab having a proximal end portion and a distal end portion, the tab having a curved protruded portion proximally extending from the proximal end portion, the curved protruded portion defining an edge, the tab being attached to the first end portion of the implant via a weld applied at the edge of the curved protruded portion, the proximal end portion of the tab having a width larger than a width of the implant, the curved protruded portion of the tab having a width smaller than the width of the implant, the tab having a first surface and a second surface opposite to the first surface, the first surface at the curved protruded portion of the tab being attached to the first end portion of the implant at the edge of the curved protruded portion, the second surface being configured to contact bodily tissue when the medical assembly is inserted to a body of a patient;
   a dilator having a first end portion and a second end portion, the first end portion of the dilator being configured to be directly coupled to the distal end portion of the tab;
   a suture having a first end portion and a second end portion, the first end portion of the suture being coupled to the second end portion of the dilator; and
   a needle directly coupled to the second end portion of the suture.

2. The medical assembly of claim 1, wherein the tab is a first tab, the medical assembly further comprising:
   a second tab configured to be attached to the second end portion of the implant.

3. The medical assembly of claim 2, wherein the dilator is a first dilator, the medical assembly further comprising:
   a second dilator configured to be coupled to the second tab.

4. The medical assembly of claim 3, wherein the suture is a first suture, the medical assembly further comprising:
   a second suture coupled to the second dilator.

5. The medical assembly of claim 4, wherein the needle is a first needle, the medical assembly further comprising:
 a second needle configured to be coupled to the second dilator through the second suture.

6. The medical assembly of claim 1, wherein the tab includes a middle portion disposed between the distal end portion of the tab and the proximal end portion of the tab, the distal end portion of the tab defining a tapered portion that tapers away from the middle portion.

7. The medical assembly of claim 6, wherein the tapered portion of the tab is coupled to the dilator, and the tapered portion of the tab does not contact any portion of the implant.

8. The medical assembly of claim 1, wherein the weld is one of a heat weld and an ultrasonic weld.

9. The medical assembly of claim 1, wherein the weld is applied only at the edge of the curved protruded portion.

10. The medical assembly of claim 1, wherein the mesh material of the implant includes polypropylene, a biologic material a combination thereof.

11. A medical assembly comprising:
 a sub-urethral implant having a first end portion and a second end portion, the sub-urethral implant including a mesh material;
 a tab including a top surface and a bottom surface, the tab including a non-mesh material, the tab being devoid of a lumen, the bottom surface of the tab configured to be removably attached to a surface of the sub-urethral implant at the first end portion of the sub-urethral implant, the top surface of the tab configured to contact a bodily tissue, the tab having a distal end portion, a proximal end portion, a middle portion disposed between the distal end portion of the tab and the proximal end portion of the tab, and a curved protruded portion extending proximally from the proximal end portion of the tab, the curved protruded portion having a width that is smaller than a width of the middle portion, the width of the curved protruded portion being smaller than a width of the sub-urethral implant, the proximal end portion of the tab having a width that is larger than the width of the sub-urethral implant, the distal end portion defining a tapered portion that tapers away from the middle portion, the curved protruded portion defining an edge, the tab being attached to the first end portion of the sub-urethral implant via a weld applied at the edge of the curved protruded portion;
 a dilator having a first end portion and a second end portion, the first end portion of the dilator being configured to be directly coupled to the distal end portion of the tab;
 a suture having a first end portion and a second end portion, the first end portion of the suture being coupled to the second end portion of the dilator; and
 a needle directly coupled to the second end portion of the suture.

12. The medical assembly of claim 11, wherein the middle portion of the tab includes lateral edges, and the lateral edges of the middle portion of the tab extend beyond lateral edges of the sub-urethral implant at the first end portion of the sub-urethral implant.

13. The medical assembly of claim 11, wherein the tab is a first tab, the medical assembly further comprising:
 a second tab including a top surface and a bottom surface, the second tab being devoid of a lumen, the bottom surface of the second tab configured to be attached to a surface of the sub-urethral implant at the second end portion of the sub-urethral implant through a heat or an ultrasonic weld applied only at an edge of the second tab.

14. The medical assembly of claim 13, wherein the dilator is a first dilator, and the suture is a first suture, the medical assembly further comprising:
 a second dilator coupled to the second tab; and
 a second suture coupled to the second dilator.

15. The medical assembly of claim 11, wherein each of the curved protruded portion, the middle portion, and the tapered portion of the tab define a different shape.

16. The medical assembly of claim 11, wherein the weld is applied only at the edge of the curved protruded portion.

17. A method for placing an implant in a body of a patient, the method comprising:
 inserting the implant inside the body of the patient through a vaginal incision, the implant being coupled to a tab via a weld at an end portion of the implant, the tab having a distal end portion, a proximal end portion, a middle portion disposed between the distal end portion of the tab and the proximal end portion of the tab, and a curved protruded portion extending proximally from the proximal end portion of the tab, the distal end portion defining a tapered portion that tapers away from the middle portion, the curved protruded portion having a width that is smaller than a width of the implant, the proximal end portion of the tab having a width that is larger than the width of the implant, the curved protruded portion defining an edge, the tab being attached to the end portion of the implant via the weld applied at the edge of the curved protruded portion, the dilator having a first end portion and a second end portion, the tapered portion of the tab being directly coupled to the first end portion of the dilator, the second end portion of the dilator being coupled to a first end portion of a suture, a second end portion of the suture being coupled to a needle;
 placing the implant under a urethra of the patient to provide support to the urethra;
 decoupling the tab from the implant by holding a middle portion of the implant and pulling the suture; and
 removing the tab out from the patient's body.

18. The method of claim 17, wherein the middle portion of the tab defines a rectangle having a width greater than the width of the implant, and the tapered portion of the tab extends from the middle portion in a direction away from the implant.

19. The method of claim 17, wherein the weld is applied only at the edge of the curved protruded portion.

20. The method of claim 17 further comprising:
 removing the dilator from the patient's body but leaving the implant within the body of the patient.

* * * * *